(12) United States Patent
Blair

(10) Patent No.: US 9,573,876 B2
(45) Date of Patent: Feb. 21, 2017

(54) RETRO-ALDOL REACTION PRODUCTS AND METHODS OF MAKING AND USING SAME

(71) Applicant: UNIVERSITY OF CENTRAL FLORIDA RESEARCH FOUNDATION, Orlando, FL (US)

(72) Inventor: Richard Blair, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/773,372

(22) PCT Filed: Mar. 7, 2014

(86) PCT No.: PCT/US2014/022045
§ 371 (c)(1),
(2) Date: Sep. 7, 2015

(87) PCT Pub. No.: WO2014/138666
PCT Pub. Date: Sep. 12, 2014

(65) Prior Publication Data
US 2016/0122275 A1    May 5, 2016

(51) Int. Cl.
| | | |
|---|---|---|
| *C07C 51/16* | (2006.01) | |
| *C07C 45/00* | (2006.01) | |
| *C07C 65/21* | (2006.01) | |
| *B01J 23/10* | (2006.01) | |
| *C07C 45/60* | (2006.01) | |
| *C07C 47/58* | (2006.01) | |

(52) U.S. Cl.
CPC ............... *C07C 65/21* (2013.01); *B01J 23/10* (2013.01); *C07C 45/60* (2013.01); *C07C 47/58* (2013.01); *C07C 51/16* (2013.01)

(58) Field of Classification Search
CPC ................................ C07C 51/16; C07C 45/00
USPC .................. 568/386, 442, 868, 869; 562/418
See application file for complete search history.

(56) References Cited

U.S. PATENT DOCUMENTS

| | | | | |
|---|---|---|---|---|
| 6,235,507 B1 * | 5/2001 | Muheim | ................... | C12P 7/24 435/147 |
| 8,062,428 B2 * | 11/2011 | Blair | ....................... | C07H 1/06 127/37 |
| 2011/0137085 A1 * | 6/2011 | Trahanovsky | .......... | C07C 29/00 568/386 |

OTHER PUBLICATIONS

Hick et al. Mechanocatalysis for biomass-derived chemicals and fuels. Green Chemistry, 2010, vol. 12, 468-474.*

* cited by examiner

*Primary Examiner* — Sikarl Witherspoon
(74) *Attorney, Agent, or Firm* — Fitzpatrick PC; William Fitzpatrick

(57) ABSTRACT

The presently disclosed and/or claimed inventive concept(s) relates generally to retro-aldol reaction products and methods of making and using same. More particularly, but without limitation, the methods disclosed herein for producing the retro-aldol reaction products are performed in a non-aqueous/solvent-free based process. The reaction products obtained from the process include, for example, dihydroxyacetone, glyceraldehyde, glycolaldehyde, and combinations thereof. In one particular embodiment, the process of making such retro-aldol reaction products includes, without limitation, the step of mechanocatalytically reacting a heterogeneous catalyst with one or more sugar reactants.

5 Claims, 3 Drawing Sheets

RETRO-ALDOL REACTION PRODUCTS AND METHODS OF MAKING AND USING SAME

BACKGROUND

1. Field of the Inventive Concept(s)

The presently disclosed and/or claimed inventive concept(s) relates generally to retro-aldol reaction products and methods of making and using same. More particularly, but without limitation, the methods disclosed herein for producing the retro-aldol reaction products are performed in a non-aqueous/solvent-free based process. The reaction products obtained from the process include, for example, dihydroxyacetone, glyceraldehyde, glycolaldehyde, and combinations thereof. In one particular embodiment, the process of making such retro-aldol reaction products includes, without limitation, the step of mechanocatalytically reacting a heterogeneous catalyst with one or more sugar reactants.

2. Background of the Inventive Concept(s)

The conversion of cellulosic biomass represents a potentially rich source of salable products such as glucose, dihydroxyacetone and glyceraldehyde. Markets for these biomass-based materials will expand as demand grows for non-petroleum sourced materials, for example. Current production methods utilize glycerol as a starting point. Profitability could be improved significantly by development of a scalable process using, for example, glucose or xylose as a starting point.

Dihydroxyacetone ("DHA") is a versatile three carbon building block that is extremely useful in many organic synthesis routes. (Enders et al., "The Dihydroxyacetone Unit—A versatile C3 Building Block in Organic Synthesis," Angew. Chem. Ind. 2005, 44, 1304-1325) DHA is a simple carbohydrate (i.e., a triose) having the formula $C_3H_6O_3$. Currently, DHA itself is primarily used as an ingredient in sunless tanning products. It is often derived from plant sources such as sugar beets and sugar cane, and by the fermentation of glycerin. DHA is a hygroscopic white crystalline powder and is the simplest of all ketoses and, having no chiral center, is the only ketose that has no optical activity. DHA is normally found as a dimer which is slowly soluble in an aqueous ethanol mixture. In its phosphate form, dihydroxyacetone phosphate (DHAP), it takes part in glycolysis and is an intermediate product of fructose metabolism.

Typically, DHA is prepared along with glyceraldehyde by the mild oxidation of glycerol with hydrogen peroxide and a ferrous salt as catalyst. It can also be prepared in high yield and selectivity at room temperature from glycerol using a cationic neocuproine-based palladium catalyst with oxygen or air acting as the co-oxidant. Although DHA is most commonly used as an ingredient in sunless tanning products, it has also been recognized as a key raw material for the production of specialty chemical products such as acrylic and cyclic derivatives. (See, e.g., Enders et al.) Glyceraldehyde is a structural isomer of dihydroxyacetone, i.e., a triose monosaccharide with the chemical formula $C_3H_6O_3$, and it is the simplest of all common aldoses. The name "glyceraldehyde" comes from the combination of glycerine and aldehyde, as glyceraldehyde is merely glycerine with one hydroxymethylene group changed to an aldehyde.

Glycolaldehyde ($HOCH_2$—$CH$—$O$) is the smallest possible molecule that contains both an aldehyde group and a hydroxyl group. It is the only possible diose, i.e., a 2-carbon monosaccharide. While not a true sugar, Glycoaldehyde is the simplest sugar-related molecule. Glycolaldehyde is an intermediate in the formose reaction. Glycolaldehyde is formed from many precursors, including the amino acid glycine. It can form by action of ketolase on fructose 1,6-bisphosphate in an alternate glycolysis pathway.

Mechanocatalysis or tribocatalysis is a solid-solid reaction using mechanical force without the addition of solvents, i.e., it is a non-aqueous or solvent-free catalytic reaction. Effective mechanocatalysts are mechanically robust, and possess sites that are physically accessible and chemically active. Mechanocatalytic processes also typically do not require external heat. Substantially all of the energy for the reaction comes from the pressures and frictional heating provided by the kinetic energy of milling media moving in a container. In a mechanocatalytic system, it is important that intimate contact between the catalyst and reactant is maintained. Pebble (or rolling) mills, shaker mills, attrition mills, and planetary mills are a few examples of mills that effectively "push" the catalyst into contact with the material to be treated in a mechanocatalytic process. A mechanocatalytic process for converting biomass to soluble sugars is, for example, disclosed in U.S. Ser. No. 11/935,712, the entire contents of which are hereby incorporated by reference in their entirety.

As such, disclosed and/or claimed herein are processes and methods for economically, safely, and reliably producing retro-aldol reaction products from the reaction of at least one sugar reactant with a heterogeneous catalyst. More particularly, but without limitation, the processes and methods claimed herein for producing retro-aldol reaction products are performed in a non-aqueous/solvent-free process. Also disclosed and/or claimed herein are reaction products from such a process that comprise at least one of dihydroxyacetone, glyceraldehyde, glycolaldehyde, and combinations thereof. In one particular embodiment, the process of making such retro-aldol reaction products includes, without limitation, the step of mechanocatalytically reacting at least one sugar reactant with a heterogeneous catalyst.

SUMMARY OF THE INVENTIVE CONCEPTS

The presently disclosed and/or claimed inventive concept(s) encompasses a retro-aldol reaction product produced by a non-aqueous and solvent-free catalytic reaction of at least one sugar reactant and a heterogeneous catalyst. In an alternate embodiment, the retro-aldol reaction products include at least one of dihydroxyacetone, glyceraldehyde, and glycolaldehyde. It is contemplated that the at least one sugar reactant is a hexose and/or a pentose. When the at least one sugar reactant includes a hexose, it is contemplated to be glucose. Alternatively, when the at least one sugar reactant includes a pentose, it is contemplated to be xylose. As disclosed herein, the heterogeneous catalyst may be a lanthanide metal oxide that is selected from the group consisting of $Er_2O_3$, $Ho_2O_3$, $Eu_2O_3$, $Nd_2O_3$, $Pr_2O_3$, $La_2O_3$, and combinations thereof.

The presently disclosed and/or claimed inventive concept(s) also encompasses a method for the production of a retro-aldol reaction product by catalytically reacting at least one sugar reactant and a heterogeneous catalyst in a non-aqueous and solvent-free environment for a period of time sufficient to produce the retro-aldol reaction product. In one embodiment, the retro-aldol reaction products include at least one of dihydroxyacetone, glyceraldehyde, and glycolaldehyde. It is contemplated that the at least one sugar reactant is a hexose and/or a pentose. When the at least one sugar reactant includes a hexose, it is contemplated to be glucose. Alternatively, when the at least one sugar reactant includes a pentose, it is contemplated to be xylose. As disclosed herein, the heterogeneous catalyst may be a lanthanide metal oxide that is selected from the group consisting of $Er_2O_3$, $Ho_2O_3$, $Eu_2O_3$, $Nd_2O_3$, $Pr_2O_3$, $La_2O_3$, and combinations thereof. Additionally, the presently disclosed and/or claimed inventive concept(s) also encompasses a method for the production of a retro-aldol reaction product produced by a non-aqueous and solvent-free mechanocatalytic reaction of at least one sugar reactant and a heterogeneous catalyst.

BRIEF DESCRIPTION OF THE DRAWINGS

The inventors have unexpectedly found that when a lanthanide oxide catalyst is combined with a sugar and agitated in a non-aqueous and solvent-free environment, a high yield of retro-aldol reaction products can be produced. In the process, the agitation of the sugar and the lanthanide oxide catalyst, typically in a mill, provides the kinetic energy necessary to drive the retro-aldol reaction

DETAILED DESCRIPTION OF THE INVENTIVE CONCEPT(S)

Figure 1:
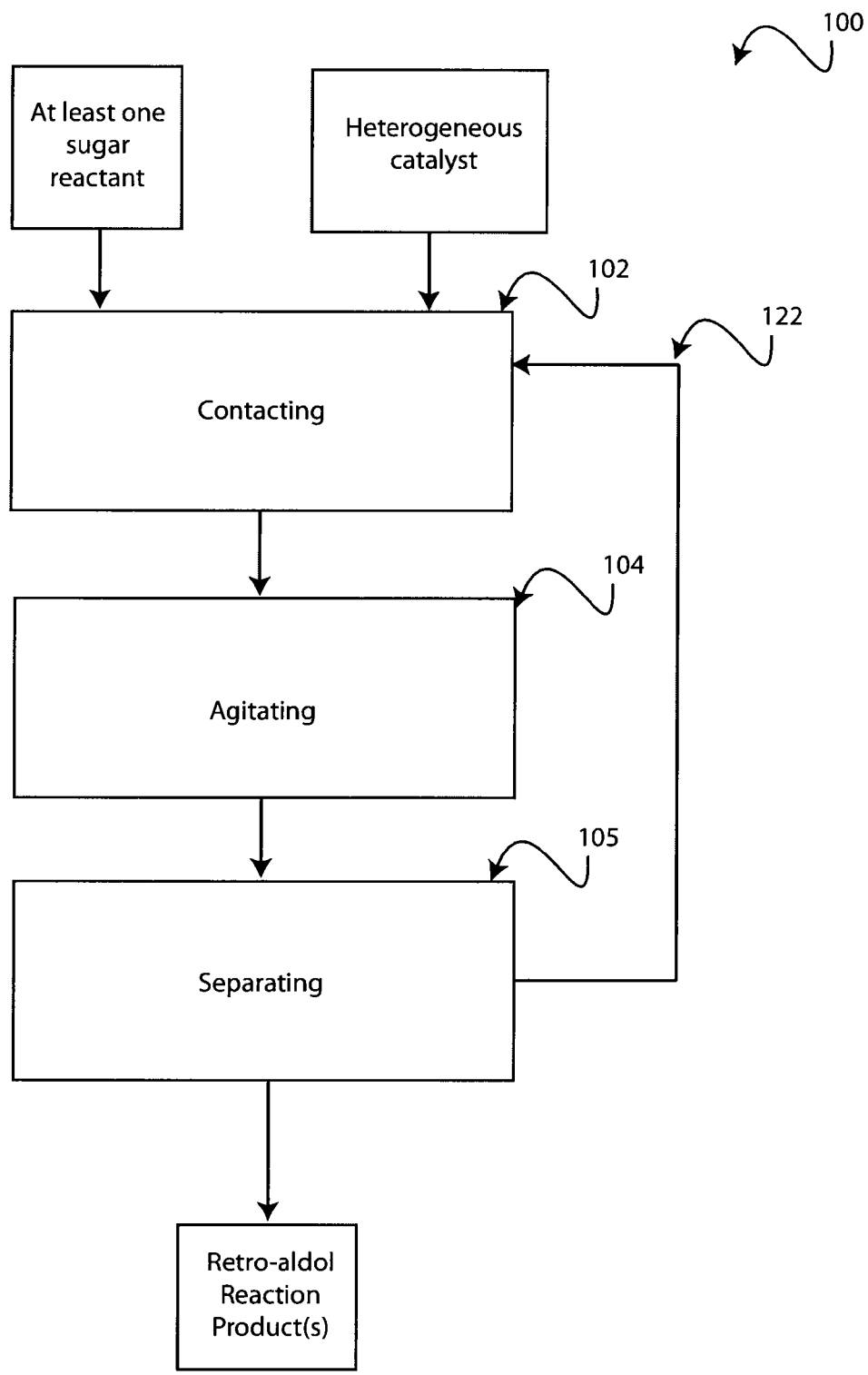
FIG. 1 is a schematic representation of a catalytic process for the production of retro-aldol reaction products from at least one sugar reactant.

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description or illustrated in the drawings. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those of skill in the art that variations may be applied to the articles and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" in may mean "one," but it is also consistent with the meaning of "one or more," "at least one," and "one or more than one." The use of the term "or" is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Now referring to the figures, FIG. 1 shows a schematic representation of a catalytic process 100 for the production of retro-aldol reaction products from at least one sugar reactant in accordance with one aspect of the presently disclosed and/or claimed inventive concept(s). More particularly, process 100 can be used to produce retro-aldol reaction products via a mechanocatalytic process using a heterogeneous catalyst. In one particular embodiment, the process 100 is used to catalyze the retro-aldol conversion of at least one sugar reactant to one or more retro-aldol reaction products comprising at least one of dihydroxyacetone, glyceraldehyde, and glycolaldehyde using a heterogeneous catalyst in a mechanocatalytic reactor. The at least one sugar reactant and the heterogeneous catalyst catalytically react under the application of mechanical force to produce such retro-aldol reaction products. In general, the process 100 is, therefore, a non-aqueous and solvent-free mechanocatalytic process for the production of retro-aldol reaction products.

In step 102, a quantity of at least one sugar reactant is contacted with a quantity of heterogeneous catalyst. To accomplish this, the materials may be introduced into any suitable vessel and, preferably, the vessel in which the step of agitating will take place in step 104, for example, by any suitable method, and simultaneously or sequentially one after the other. In all embodiments, the aggregation of the at least one sugar reactant and the heterogeneous catalyst results in a non-aqueous and solvent-free reactant mixture suitable for a non-aqueous and solvent-free retro-aldol process.

The at least one sugar reactant may be any material or mixture of materials having a saccharide content. Thus, in one embodiment, the at least one sugar reactant may be, but not by way of limitation, a monosaccharide, a disaccharide, an oligosaccharide, and/or a polysaccharide. In one embodiment, the at least one sugar reactant is a hexose such as, for example, glucose. Alternatively, the at least one sugar reactant may be a pentose such as, for example, xylose. In certain embodiments, the at least one sugar reactant may be 100 percent saccharide. For example, the at least one sugar reactant may comprise 100 percent monosaccharide, disaccharide, oligosaccharide, or polysaccharide. The at least one sugar reactant may comprise 100 percent hexose, pentose, or any percent mixture or combination thereof. In alternative embodiments, the at least one sugar reactant may comprise greater than 1, 5, 10, 20, 30, 40, 50, 60, 70, 80, 90, 95, or even 99 saccharide separated away from any contaminants and/or other reactive and non-reactive materials.

In another embodiment, the at least one sugar reactant may be a soluble sugar obtained from the hydrolysis of a natural cellulosic feedstock, typically referred to as a "biomass." One such exemplary method of creating soluble sugars from a biomass is disclosed in U.S. Ser. No. 12/621,741, entitled "SOLID ACID CATALYZED HYDROLYSIS OF CELLULOSIC MATERIALS". Exemplary biomass materials include wood, paper, switchgrass, wheat straw, agricultural plants, trees, agricultural residues, herbaceous crops, starches, corn stover, saw dust, and high cellulose municipal and industrial solid wastes. The nature or origin of the at least one sugar reactant should not be considered to be constraining to the processes and methods disclosed herein, i.e., the at least one sugar reactant is source and composition independent and one of ordinary skill in the art, given the present disclosure, would appreciate that the origin and composition of the at least one sugar reactant could be tailored or blended in such a manner to provide any number of different retro-aldol reaction products using the heterogeneous catalyst and reaction conditions disclosed herein. In one embodiment, given for exemplary purposes and not by way of limitation, the at least one sugar reactant material may be obtained from a lignocellulosic material having a cellulose, hemicellulose, and lignin content and according to any of the known processes for obtaining sugars therefrom.

The heterogeneous catalyst may be any solid material having a retro-aldol catalytic activity under the process and reaction conditions described herein. In one embodiment, such reaction conditions comprise a mechanocatalytic process. The heterogeneous catalyst functions in the same phase as the reactants and, pursuant to the presently disclosed and/or claimed inventive concept(s), the heterogeneous catalyst is in the solid phase as is the at least one sugar reactant. The reactants (i.e., the at least one sugar reactant and the heterogeneous catalyst) catalytically react with one another, therefore, in a non-aqueous and solvent-free environment.

The heterogeneous catalyst may be more particularly defined as a metal oxide. In one specific but non-limiting embodiment, the heterogeneous catalyst comprises a metal oxide containing at least one rare earth element or lanthanide compound. The term "at least one rare earth element or lanthanide compound" means one or more of the fifteen chemical elements with atomic numbers 57 through 71, from lanthanum through lutetium. The informal chemical symbol Ln is used in general discussions of lanthanide chemistry to refer to any lanthanide. All but one of the lanthanides are f-block elements, corresponding to the filling of the 4f electron shell; lutetium, a d-block element, is also generally considered to be a lanthanide due to its chemical similarities with the other fourteen. All lanthanide elements form trivalent cations, $Ln^{3+}$, whose chemistry is largely determined by the ionic radius, which decreases steadily from lanthanum to lutetium. The electronic structure of the lanthanide elements, with minor exceptions is $[Xe]6s^24f^n$. In their compounds, the 6s electrons are lost and the ions have the configuration $[Xe]4^m$. The chemistry of the lanthanides differs from main group elements and transition metals because of the nature of the 4f orbitals. These orbitals are "buried" inside the atom and are shielded from the atom's environment by the 4d and 5p electrons. As a consequence of this, the chemistry of the elements is largely determined by their size, which decreases gradually from 102 pm ($La^{3+}$) with increasing atomic number to 86 pm ($Lu^{3+}$), the so-called lanthanide contraction. All the lanthanide elements exhibit the oxidation state +3. In addition $Ce^{3+}$ can lose its single f electron to form $Ce^{4+}$ with the stable electronic configuration of xenon. Also, $Eu^{3+}$ can gain an electron to form $Eu^{2+}$ with the f7 configuration which has the extra stability of a half-filled shell. Promethium is effectively a man-made element as all its isotopes are radioactive with half-lives shorter than 20 years. In terms of reduction potentials, the $Ln^{0/3+}$ couples are nearly the same for all lanthanides, ranging from −1.99 (for Eu) to −2.35 V (for Pr). Thus, these metals are highly reducing, with reducing power similar to alkaline earth metals such as Mg (−2.36 V). According to the concept of hard and soft acids and bases (HSAB) established by Pearson, lanthanide +3 ions are considered to be hard acids, falling between Mg(II) and Ti(IV) in the established scale. Lanthanides therefore complex preferentially to hard bases such as oxygen donor ligands. The strong affinity of lanthanides for oxygen is further evidenced by the bond dissociation energies for the gas phase dissociation of diatomic lanthanide oxides (LnO). For example, although they are among the lowest values for lanthanides, both SmO (136 kcal/mol; 1 cal=4.18 J) and Yb (95 kcal/mol) exhibit values significantly higher than that for MgO (86 kcal/mol).

In one embodiment, the heterogeneous catalyst is a lanthanide metal oxide or rare earth metal oxide. Exemplary lanthanide oxides that may comprise the heterogeneous catalyst for use in the presently disclosed and/or claimed inventive concept(s) include Erbium oxide ($Er_2O_3$) and/or Neodymium oxide ($Nd_2O_3$) although one of ordinary skill in the art will appreciate that any lanthanide metal oxide may be used in the process of the presently disclosed and/or claimed inventive concept(s). The heterogeneous catalyst may comprise up to 100 weight percent of a single lanthanide metal oxide. In other embodiments, the heterogeneous catalyst may comprise at least two lanthanide metal oxides in varying weight percent amounts. Additionally, the heterogeneous catalyst may comprise one or more non-catalytically active substrate or support materials. As such, it should be appreciated by one of ordinary skill in the art that it is preferable that the heterogeneous catalyst comprise a catalytic material containing a catalytically active amount of a lanthanide oxide such as, but not by way of limitation, Erbium oxide and/or Neodymium oxide.

Without wishing to be bound by any particular method of reaction, it is believed that the lanthanide oxides are particularly useful as the heterogeneous catalyst for use in the presently disclosed and/or claimed inventive concept(s) because the surface metal sites form complexes with the keto and alcohol groups in saccharides facilitating the retro aldol conversion. In the presently disclosed and/or claimed inventive concept(s), it is believed that the agitating step 104 (as described herein) provides the kinetic energy and pressures necessary for catalysis to occur. As such, the heterogeneous catalyst is capable of converting pentoses, hexoses, and heptoses to 2 and 3 carbon fragments.

Although the at least one sugar reactant and/or the heterogeneous catalyst may have an inherent water content, it should be understood that the reactants,—either alone or in combination—are still to be considered in a solid or non-aqueous phase. It should be understood, however, that the existence of such an amount of inherent water in the reactants should not be interpreted to mean that the reaction (i.e., the agitating step 104) occurs in an aqueous environment: rather, while some minor amount of water may be present, the mechanocatalytic reaction between the at least one sugar reactant and the heterogeneous catalyst is carried out in a non-aqueous and solvent-free environment and the at least one sugar reactant and the heterogeneous catalyst should be understood to be in a solid form. In one embodiment, when the at least one sugar reactant and the heterogeneous catalyst are contacted in step 102 and agitated in step 104, the free water content of the collective mixture of the reactants (i.e., the inherent water of the at least one sugar reactant and the heterogeneous catalyst) is less than about 45% by weight of the materials (thereby maintaining the reactants in a solid and/or non-aqueous environment) and, more preferably, the free water content of the collective mixture of the reactants is less than about 30% by weight, less than about 20% by weight, less than about 10% by weight, and from about less than about 5% by weight.

The ratio of the at least one sugar reactant to the heterogeneous catalyst is such that the formation of retro-aldol reaction products is optimized. Generally, the catalytic efficiency is optimized by determining a ratio of the at least one sugar reactant to the heterogeneous catalyst, wherein a surface interaction of the at least one sugar reactant and the heterogeneous catalyst is maximized and the production of specified or targeted retro-aldol reaction products is optimized. In one embodiment, but not by way of limitation, the at least one sugar reactant and the heterogeneous catalyst are provided in a ratio of from about 4:1 to about 1:1 and, more particularly, from about 2:1 to about 1:1.

It is also contemplated that the process 100 is preferably performed at ambient temperature but may also occur at any temperature in a range of from about −5° C. to 146° C. Although the term "ambient temperature" should be understood as the purposeful absence of external heating or cooling, it is also contemplated that the reactants and reaction mixture may autogenously provide additional heat through exothermic reactions and such a process is also considered for the purposes of this disclosure as occurring at "ambient temperature". Additionally, it is contemplated that the process 100 be performed without the addition of water or other solvent to the reactant mixture. Of course, although the process is disclosed and described as occurring in a non-aqueous and solvent-free environment, the water content of the reactant mixture may be up to about 40% by weight and yet still be considered as comprising a non-aqueous and solvent-free mixture. As such, it may be desirable in some situations to add some amount of water to the reactant mixture in order to maintain the amount of water within the reactant mixture to less than or about 40% by weight.

As would be readily apparent to one of ordinary skill, the ability to perform the process 100 according to the presently disclosed and/or claimed inventive concept(s) provides an efficient and effective means of producing retro-aldol reaction products including at least dihydroxyacetone, glyceraldehyde, glycolaldehyde, from at least one sugar reactant using a heterogeneous catalyst in a non-aqueous and solvent-free environment on a large commercial batch or continuous manufacturing scale.

In step 104, the at least one sugar reactant and the heterogeneous catalyst are agitated for a time sufficient to provide a reaction product containing solid, powdered, and/or liquid retro-aldol reaction products. The agitation may take place in any suitable vessel or reactor. In one embodiment, the agitating step 104 takes place in a ball, roller, jar, hammer, attrition, or shaker mill. The mills generally grind the reactants by placing them in a housing along with one or more grinding elements and imparting motion to the housing. The housing is typically cylindrical in shape and the grinding elements and/or milling media (as discussed herein) are typically steel balls, but may also be rods, cylinders, or other shapes. The containers and grinding elements can be made from the same material. Milling media may be, for example but not by way of limitation, 440C stainless steel balls ½ inch in diameter. As used herein, the term "milling" should be understood to be the agitating step 104 wherein the reactants (i.e., the at least one sugar reactant and the heterogeneous catalyst) are brought into contact with one another as well as with the milling media within the reactor. During the agitation step 104, the reactants catalytically react to form the retro-aldol reaction products. Once again, the reactants and the milling media are agitated in step 104 in a substantially non-aqueous and solvent-free environment and in a solid state.

As the container is rolled, swung, vibrated, or shaken, the inertia of the grinding elements and/or milling media causes the milling media to move independently into each other and against the container wall, grinding the at least one sugar reactant and the heterogeneous catalyst thereby bringing the reactants into reactive contact with one another. In one embodiment, the mill is a shaker mill using steel balls as the milling media and shaking to agitate the at least one sugar reactant and the heterogeneous catalyst. The mills for use in the presently disclosed and/or claimed inventive concept(s)

may range from those having a sample capacity of a gram or less to large industrial mills with a throughput of tons per minute. Such mills are available from SPEX CertiPrep of Metuchen, N.J., for example, Paul O. Abbe, Bensenville, Ill., or Union Process Inc., Akron, Ohio. For some mills, such as a steel ball mill from Paul O. Abbe, the optimal fill volume is about 25% of the total volume of the mill. The number of steel balls (i.e., the milling media) required for the process 100 is typically dependent upon the amount of kinetic energy available. High energy milling like that in a shaker mill will require less milling media than lower energy milling methods such as rolling mills. For shaking mills, a ball to sample mass ratio (i.e., a milling media to reactant mass ratio) of about 12:1 is sufficient. For rolling mills, a ball to sample mass ratio (i.e., a milling media to reactant mass ratio) of about 30:1 at a rolling rate sufficient to maintain tumbling of the milling media is acceptable for use. Lower mass ratios can be obtained by increasing the amount of kinetic energy available to the system. In a roller mill, this can be achieved through the optimization of mill geometry and the rotational velocity of the mill.

A significant advantage of the presently disclosed and/or claimed inventive concept(s) is that the processes described herein can be performed at ambient temperature without the need for added heat, cooling, or modifying pressure. Instead, the processes, including the agitation step 104, can be performed under ambient conditions. Without wishing to be bound by theory, it is believed the agitating step 104 of the at least one sugar reactant with the heterogeneous catalyst, such as in with the aforementioned mills, provides the process with the kinetic energy required for catalysis. Moreover, it is further believed that the agitating step 104 also allows more of the at least one sugar reactant to come into contact with catalytic sites on the heterogeneous catalyst. Even further, it is believed that the heat created by the agitating step 104 facilitates the depolymerization of the saccharide while bound to open metal sites on the lanthanide oxide. In one embodiment, the agitating step 104 may occur at a controlled temperature of between about −5 to about 146 degrees C. It is contemplated that the agitating step 104 may occur at any temperature degree value within this range (rounded to the nearest 0.5 centigrade unit), or within any sub-ranges within this range (rounded to the nearest 0.5 centigrade unit).

After the step of agitating 104, the retro-aldol reaction products may be separated from any unreacted at least one sugar reactant and/or heterogeneous catalyst (as well as any other contaminants and/or other unreactive components) in step 105. Typically, the retro-aldol reaction products obtained after the step of agitating 104 comprises at least one of dihydroxyacetone, glyceraldehyde, glycolaldehyde, and combinations thereof. The reaction products may be in a solid, semi-solid, or liquid state, although in a preferred but not limiting embodiment, it is contemplated that the reaction products will be substantially in a solid state. For example, dihydroxyacetone is a solid while racemic glyceraldehyde is a liquid. As such, the at least one sugar reactant undergoes liquefaction in producing the reaction product glyceraldehyde.

When using a mill as described herein, the mechanocatalytic processes described are generally carried out as a batch process. In addition, the vessel where the agitating and retro-aldol reaction takes place may be performed in a continuous attritter, which is commercially available from Union Process, Akron, Ohio. This device more generally allows the process to be carried out as a continuous process.

The milling time performed in the agitating step 104 may have an effect on the extent of catalytic conversion of the at least one sugar reactant into the retro-aldol reaction products. It is contemplated that from at least about 100% to about 5% of the at least one sugar reactant will be catalyzed to form the retro-aldol reaction product in various embodiments of the presently disclosed and/or claimed inventive concept(s). It is appreciated that higher or lower efficiencies of the catalytic conversion of the at least one sugar reactant to retro-aldol reaction products may be obtained by selecting from the various heterogeneous catalysts (discussed herein), milling time, and by modifying the ratio of the at least one sugar reactant to the heterogeneous catalyst.

Referring again to FIG. 1, after step 104 of agitating, the retro-aldol reaction products may be separated via the separating step 105 in order to provide individual compounds (i.e., the retro-aldol reaction products) which may be quantitated and/or used in the preparation of other chemicals of interest. Any suitable method of determining the amount of retro-aldol reaction product may be used, such as by chromatographic methods well known in the art. Moreover, the presence of particular retro-aldol reaction products may be confirmed by any suitable chromatography method, such as thin-layer chromatograph, gas chromatography (GC), high-pressure liquid chromatography (HPLC), GC-MS, LC-MS, or any other suitable method known in the art. The retro-aldol reaction products may be separated out individually and stored. Alternatively, at least a portion of the retro-aldol reaction products may be sent to a subsequent processing step prior to separating out individual retro-aldol reaction products from one another. In either event, one or more of the retro-aldol reaction products (either individually or in a mixture) may be sent to a secondary process to convert the retro-aldol reaction products into secondary products. For example, but not by way of limitation, such secondary products may comprise polypropylene, propylene glycol, acetone, plastics, fibers, and pharmaceutical compounds.

Since the heterogeneous catalyst is acting as a catalyst (and not as a chemical reactant) in the retro-aldol conversion of the at least one sugar reactant, the heterogeneous catalyst may be recycled in whole or in part. Thus, optionally, the heterogeneous catalyst (as a separated product and/or in combination with the reaction products leaving step 104) may be directed to recycling step 122 to prepare the heterogeneous catalyst for reuse in subsequent contacting step(s) 102 and/or agitating step(s) 104. If no preparation step is necessary for the recycling of the heterogeneous catalyst, the heterogeneous catalyst material can be immediately reused in contacting step 102. In either instance, the heterogeneous catalyst is optionally recycled and reused to catalyze further at least one sugar reactant to retro-aldol reaction products by starting the process again at step 102 and/or step 104. Additional heterogeneous catalyst may be added as needed to supplement the recycled heterogeneous catalyst when repeating steps 102 and/or 104. Accordingly, a significant advantage of the presently disclosed and/or claimed inventive concept(s) is that at least a portion of the heterogeneous catalyst may be reused continuously, thereby saving considerable material and expense.

Examples

Figure 2:
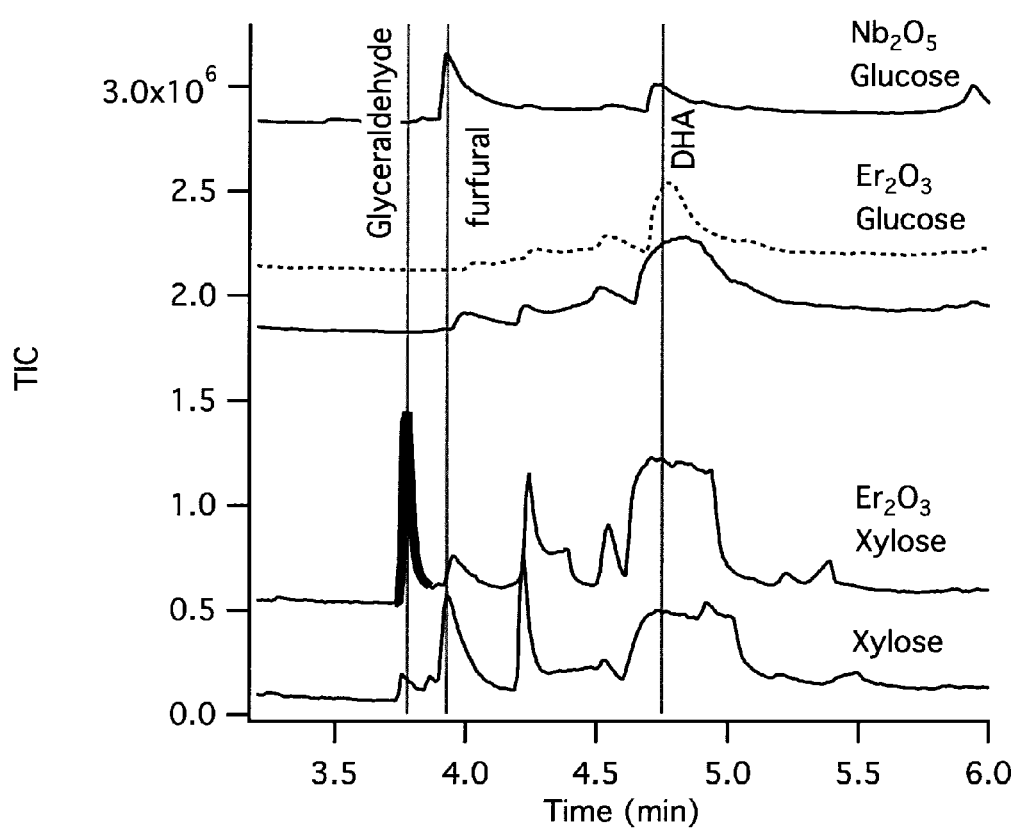
FIG. 2 is a graphical representation of the retro-aldol reaction products produced according to the process shown in FIG. 1.
Figure 3:
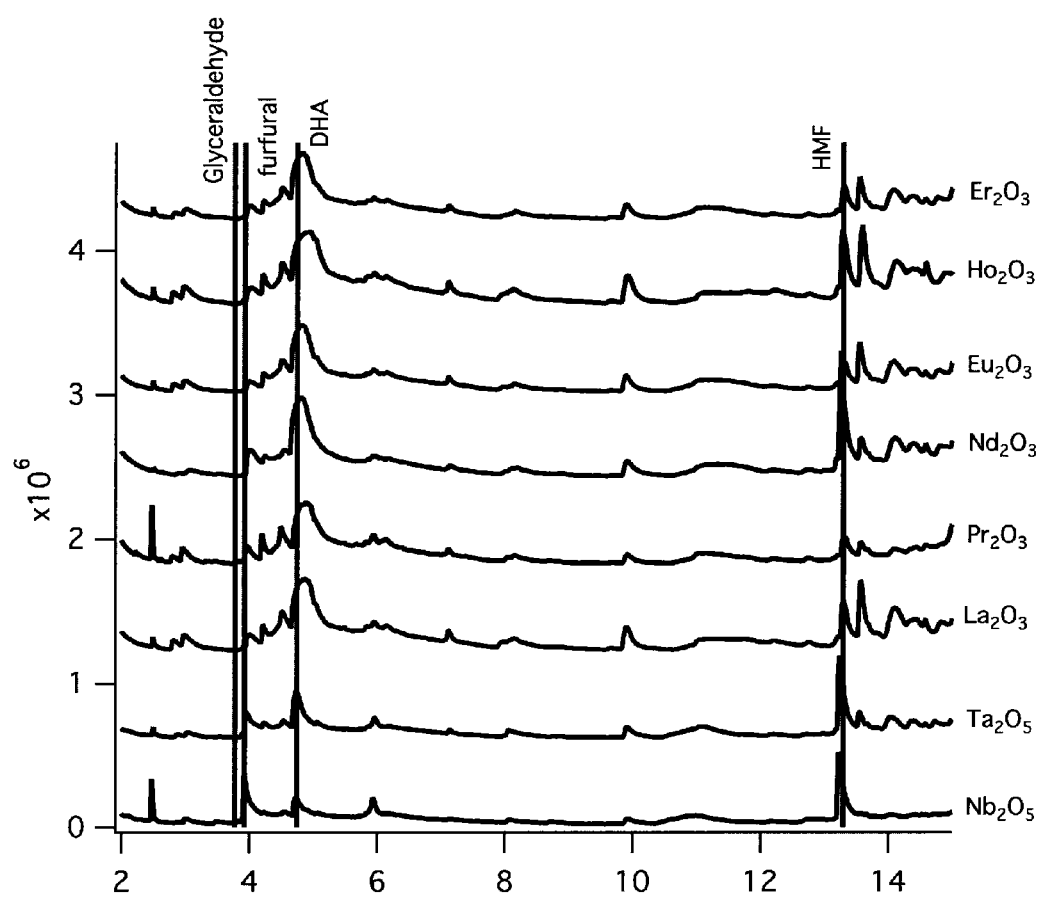
FIG. 3 is a graphical representation of additional retro-aldol reaction products produced according to the process shown in FIG. 1.

As shown in FIGS. 2 and 3, retro-aldol catalytic reactions of the at least one sugar reactant and the heterogeneous catalyst (collectively, "reactants") were performed in, and agitation was supplied by, a SPEX 8000D mixer mill (SPEX CertiPrep, Metuchen, N.J.). A 1:1 mixture of at least one sugar reactant and heterogeneous catalyst were investigated and, more particularly, 1 gram of at least one sugar reactant and 1 gram of heterogeneous catalyst were milled in hardened steel vials with 0.5" steel balls (i.e., milling media) and a ball to sample mass ratio (i.e., mass of the milling media to the mass of the reactants) of 12:1.

As can be appreciated from FIGS. 2 and 3, the retro-aldol catalytic reactions were carried out with the at least one sugar comprising either glucose (Fisher Scientific, Certified ACS) or xylose (Acros Organics, 99+%) and the homogeneous catalyst being lanthanide metal oxides of $Er_2O_3$ (Laguna Clay Company), $Ho_2O_3$ (MTI corporation, +99.999%), $Eu_2O_3$ MTI corporation, +99.995%), $Nd_2O_3$ (Alfa Aesar, 99.9%), $Pr_2O_3$ (Laguna Clay Company), and $La_2O_3$ (Alfa Aesar, 99.99%). For purpose of comparison, two transition metal oxides were also tested for use as the heterogeneous catalyst: $Ta_2O_5$ (Alfa Aesar, 99%) and $Nb_2O_5$ (Ventron, 99.9%).

One retro-aldol catalytic reaction was performed with glucose (Fisher Scientific, Certified ACS) being the at least one sugar reactant and $Er_2O_3$ (Laguna Clay Company) being the heterogeneous catalyst (more particularly, 1 gram of glucose and 1 gram of $Er_2O_3$ were used) in a 1:1 mixture in a custom pebble mill with a gas-tight milling container constructed of 304 stainless steel. (The results being shown in the dashed line of FIG. 2) The custom pebble mill was shaped as a double truncated cone to ensure adequate tumbling of the milling media. Conflat flanges with silicone O-rings and Deublin rotary feedthroughs with Kalrez O-rings and Krytox lubricant were used to maintain gas tight conditions during operation. Stainless steel frits (Applied Porous Materials) were fitted to the entry and exit feedthroughs to eliminate the accumulation of dust in the sealing surfaces of the feedthroughs. Spherical milling media of 3 balls of 0.5" in diameter (440C stainless steel) was added to the mixture of the at least one sugar reactant and the heterogeneous catalyst. Pressure was monitored with a NOSHOK pressure transducer and controlled with a MicroMod 53MC5000 loop controller. The mill's rotational speed was controlled with a ⅓ hp variable speed DC motor. The reaction in the pebble mill was carried out for two hours at ambient temperature, a pressure of 1 atmosphere, and a rotational speed of 270 RPM.

1. Gas Chromatography with Mass Sensitive Detection

GC-MS analysis was performed on an Agilent 6850 GC with an Agilent 19091-433E HP-5MS column (5% phenyl methyl siloxane, 30 m×250 μm×0.25 μm nom.) coupled with a 5975C VL mass selective detector. Samples were pulled from the reactor, dissolved in methanol and filtered through a Whatman 0.2 μm PTFE syringe filter before injection.

When the reaction products were analyzed by GC/MS, it was found that heterogeneous catalysts generally produce a product composition similar to those produced when $Er_2O_3$ (FIG. 2) was used as a catalyst. The exception was $Nd_2O_3$ which also produced dehydration products. In contrast, main group oxides (e.g., CaO) produced no detectable products while transition metal oxides (e.g., $Nb_2O_3$ and $Ta_2O_3$) produced mainly the dehydration products 5-hydroxymethylfurfural and furfural. All heterogeneous catalysts gave some retro aldol products and neodymium oxide also produced dehydration products.

The presently disclosed and/or claimed inventive concept(s), in various embodiments, includes components, methods, processes, systems and/or apparatus substantially as depicted and described herein, including various embodiments, subcombinations, and subsets thereof. Those of skill in the art will understand how to make and use the presently disclosed and/or claimed inventive concept(s) after understanding the present disclosure. The presently disclosed and/or claimed inventive concept(s), in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the presently disclosed and/or claimed inventive concept(s) has been presented for purposes of illustration and description. The foregoing is not intended to limit the presently disclosed and/or claimed inventive concept(s) to the form or forms disclosed herein. In the foregoing Detailed Description for example, various features of the presently disclosed and/or claimed inventive concept(s) are grouped together in one or more embodiments for the purpose of streamlining the disclosure. This method of disclosure is not to be interpreted as reflecting an intention that the claimed presently disclosed and/or claimed inventive concept(s) requires more features than are expressly recited in each claim. Rather, as the following claims reflect, presently disclosed and/or claimed inventive concept(s) lie in less than all features of a single foregoing disclosed embodiment. Thus, the following claims are hereby incorporated into this Detailed Description, with each claim standing on its own as a separate preferred embodiment of the presently disclosed and/or claimed inventive concept(s).

Moreover, though the description of the presently disclosed and/or claimed inventive concept(s) has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for the production of an oxidized reaction product, comprising the step of catalytically reacting an amount of a polymer containing material and an oxidation catalyst in a non-aqueous and solvent-free environment for a period of time sufficient to produce the oxidized reaction product
wherein the oxidation catalyst is at least one of a solid metal oxide, a layered porphyrin-like material, and combinations thereof;
wherein the solid metal oxide comprises at least one of manganese oxides, cerium oxides, copper oxides, silver oxides, and combinations thereof.

2. The method of claim 1, wherein the oxidation catalyst comprises a solid metal oxide comprising at least one of manganese oxides, cerium oxides, and combinations thereof.

3. The method of claim 1 wherein the oxidation catalyst comprises K-Birnessite.

4. The method of claim 1, wherein the oxidation catalyst comprises a layered porphyrin-like material.

5. The method of claim 4, wherein the oxidation catalyst comprises hexagonal carbon nitride.

\* \* \* \* \*